US006633234B2

(12) United States Patent
Wiener et al.

(10) Patent No.: US 6,633,234 B2
(45) Date of Patent: Oct. 14, 2003

(54) METHOD FOR DETECTING BLADE BREAKAGE USING RATE AND/OR IMPEDANCE INFORMATION

(75) Inventors: Eitan T. Wiener, Cincinnati, OH (US); Foster B. Stulen, Mason, OH (US); Allan L. Friedman, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 145 days.

(21) Appl. No.: 09/864,089

(22) Filed: May 24, 2001

(65) Prior Publication Data

US 2002/0049427 A1 Apr. 25, 2002

Related U.S. Application Data

(60) Provisional application No. 60/242,273, filed on Oct. 20, 2000.

(51) Int. Cl.[7] ............................................. G08B 21/00
(52) U.S. Cl. .................... 340/680; 340/683; 340/506; 702/106; 702/64; 702/65; 702/74; 702/75; 702/81; 702/82
(58) Field of Search ................................. 340/680, 679, 340/683, 506, 3.1; 702/106, 66, 107, 171, 65, 64, 74, 75, 81, 82; 606/169, 41

(56) References Cited

U.S. PATENT DOCUMENTS

| | | | |
|---|---|---|---|
| 2,917,691 A | 12/1959 | DePrisco et al. ............ 318/118 |
| 4,546,773 A * | 10/1985 | Kremer et al. ............... 600/452 |
| 4,567,769 A * | 2/1986 | Barkhoudarian .............. 73/643 |
| 4,608,019 A * | 8/1986 | Kumabe et al. ............. 433/118 |
| 5,001,649 A | 3/1991 | Lo et al. ...................... 364/484 |
| 5,026,387 A | 6/1991 | Thomas ....................... 606/169 |
| 5,112,300 A | 5/1992 | Ureche ......................... 604/22 |
| 5,180,363 A | 1/1993 | Idemoto et al. .............. 202/32 |
| 5,209,719 A * | 5/1993 | Baruch et al. ................. 604/22 |
| 5,387,190 A | 2/1995 | Gotanda et al. .............. 604/22 |
| 5,400,267 A | 3/1995 | Denen et al. ................ 364/552 |
| 5,425,704 A | 6/1995 | Sakurai et al. ................ 604/22 |
| 5,449,370 A | 9/1995 | Vaitekunas .................. 606/169 |
| 5,630,420 A | 5/1997 | Vaitekunas ............. 128/662.03 |
| 5,707,369 A | 1/1998 | Vaitekunas et al. ........... 606/31 |
| 5,842,102 A * | 11/1998 | Montfort et al. ............ 399/349 |
| 5,879,364 A | 3/1999 | Bromfield et al. .......... 606/169 |
| 5,968,007 A | 10/1999 | Simon et al. .................. 604/22 |
| 6,017,354 A | 1/2000 | Culp et al. ................... 606/170 |
| 6,019,775 A | 2/2000 | Sakurai ....................... 606/169 |
| 6,024,750 A * | 2/2000 | Mastri et al. ................ 606/169 |
| 6,036,667 A * | 3/2000 | Manna et al. .................. 604/22 |
| 6,063,050 A * | 5/2000 | Manna et al. .................. 604/22 |
| 6,066,135 A | 5/2000 | Honda .......................... 606/39 |
| 6,090,123 A | 7/2000 | Culp et al. ................... 606/180 |
| 6,293,754 B1 * | 9/2001 | Liang et al. .................... 416/1 |
| 6,480,796 B2 * | 11/2002 | Wiener ........................ 702/106 |

FOREIGN PATENT DOCUMENTS

| | | |
|---|---|---|
| JP | 2000-175926 | 6/2000 |
| WO | WO95/09572 | 4/1995 |

\* cited by examiner

*Primary Examiner*—Daryl Pope
(74) *Attorney, Agent, or Firm*—Darby & Darby

(57) ABSTRACT

Failures associate with bad hand pieces and blade failures in an ultrasonic surgical system are distinguished by monitoring the rate of change of the resonance frequency and the rate of change of the resonance impedance of the hand piece/blade as the drive frequency is changed. As the system reaches resonance, the control system locks onto the resonance frequency. When a loss of lock occurs with no recovery, the rate of change of the frequency and rate of change of the impedance are compared to obtain the fastest rate of change which is stored in non-volatile memory of the ultrasonic generator. If the rates of change are higher than normal rates of change due to temperature changes with the longest blades, a "Bad Blade" message is displayed on an LCD.

9 Claims, 6 Drawing Sheets

METHOD FOR DETECTING BLADE BREAKAGE USING RATE AND/OR IMPEDANCE INFORMATION

RELATED APPLICATIONS

The present invention relates to, and claims priority of, U.S. Provisional Patent Application Ser. No. 60/242,273 filed on Oct. 20, 2000, having the same title as the present invention, which is incorporated herein by reference.

BACKGROUND OF THE INVENTION

1. Field of the Invention

The present invention generally relates to ultrasonic surgical systems and, more particularly, to a method for detecting blade breakage using rate information and/or impedance information.

2. Description of the Related Art

It is known that electric scalpels and lasers can be used as a surgical instrument to perform the dual function of simultaneously effecting the incision and hemostatis of soft tissue by cauterizing tissues and blood vessels. However, such instruments employ very high temperatures to achieve coagulation, causing vaporization and fumes as well as splattering, which increases the risk of spreading infectious diseases to operating room personnel. Additionally, the use of such instruments often results in relatively wide zones of thermal tissue damage.

Cutting and cauterizing of tissue by means of surgical blades vibrated at high speeds by ultrasonic drive mechanisms is also well known. One of the problems associated with such ultrasonic cutting instruments is uncontrolled or undamped vibrations and the heat as well as material fatigue resulting therefrom. In an operating room environment attempts have been made to control this heating problem by the inclusion of cooling systems with heat exchangers to cool the blade. In one known system, for example, the ultrasonic cutting and tissue fragmentation system requires a cooling system augmented with a water circulating jacket and means for irrigation and aspiration of the cutting site. Another known system requires the delivery of cryogenic fluids to the cutting blade.

It is known to limit the current delivered to the transducer as a means for limiting the heat generated therein. However, this could result in insufficient power to the blade at a time when it is needed for the most effective treatment of the patient. U.S. Pat. No. 5,026,387 to Thomas, which is assigned to the assignee of the present application and is incorporated herein by reference, discloses a system for controlling the heat in an ultrasonic surgical cutting and hemostasis system without the use of a coolant, by controlling the drive energy supplied to the blade. In the system according to this patent an ultrasonic generator is provided which produces an electrical signal of a particular voltage, current and frequency, e.g. 55,500 cycles per second. The generator is connected by a cable to a hand piece which contains piezoceramic elements forming an ultrasonic transducer. In response to a switch on the hand piece or a foot switch connected to the generator by another cable, the generator signal is applied to the transducer, which causes a longitudinal vibration of its elements. A structure connects the transducer to a surgical blade, which is thus vibrated at ultrasonic frequencies when the generator signal is applied to the transducer. The structure is designed to resonate at the selected frequency, thus amplifying the motion initiated by the transducer.

The signal provided to the transducer is controlled so as to provide power on demand to the transducer in response to the continuous or periodic sensing of the loading condition (tissue contact or withdrawal) of the blade. As a result, the device goes from a low power, idle state to a selectable high power, cutting state automatically depending on whether the scalpel is or is not in contact with tissue. A third, high power coagulation mode is manually selectable with automatic return to an idle power level when the blade is not in contact with tissue. Since the ultrasonic power is not continuously supplied to the blade, it generates less ambient heat, but imparts sufficient energy to the tissue for incisions and cauterization when necessary.

The control system in the Thomas patent is of the analog type. A phase lock loop (that includes a voltage controlled oscillator, a frequency divider, a power switch, a matching network and a phase detector), stabilizes the frequency applied to the hand piece. A microprocessor controls the amount of power by sampling the frequency, current and voltage applied to the hand piece, because these parameters change with load on the blade.

The power versus load curve in a generator in a typical ultrasonic surgical system, such as that described in the Thomas patent, has two segments. The first segment has a positive slope of increasing power as the load increases, which indicates constant current delivery. The second segment has a negative slope of decreasing power as the load increases, which indicates a constant or saturated output voltage. The regulated current for the first segment is fixed by the design of the electronic components and the second segment voltage is limited by the maximum output voltage of the design. This arrangement is inflexible since the power versus load characteristics of the output of such a system can not be optimized to various types of hand piece transducers and ultrasonic blades. The performance of traditional analog ultrasonic power systems for surgical instruments is affected by the component tolerances and their variability in the generator electronics due to changes in operating temperature. In particular, temperature changes can cause wide variations in key system parameters such as frequency lock range, drive signal level, and other system performance measures.

In order to operate an ultrasonic surgical system in an efficient manner, during startup the frequency of the signal supplied to the hand piece transducer is swept over a range to locate the resonance frequency. Once it is found, the generator phase lock loop locks on to the resonance frequency, continues to monitor the transducer current to voltage phase angle, and maintains the transducer resonating by driving it at the resonance frequency. A key function of such systems is to maintain the transducer resonating across load and temperature changes that vary the resonance frequency. However, these traditional ultrasonic drive systems have little to no flexibility with regards to adaptive frequency control. Such flexibility is key to the system's ability to discriminate undesired resonances. In particular, these systems can only search for resonance in one direction, i.e., with increasing or decreasing frequencies and their search pattern is fixed. The system cannot: (i) hop over other resonance modes or make any heuristic decisions, such as what resonance to skip or lock onto, and (ii) ensure delivery of power only when appropriate frequency lock is achieved.

The prior art ultrasonic generator systems also have little flexibility with regard to amplitude control, which would allow the system to employ adaptive control algorithms and decision making. For example, these fixed systems lack the ability to make heuristic decisions with regards to the output drive, e.g., current or frequency, based on the load on the blade and/or the current to voltage phase angle. It also limits the system's ability to set optimal transducer drive signal levels for consistent efficient performance, which would increase the useful life of the transducer and ensure safe operating conditions for the blade. Further, the lack of control over amplitude and frequency control reduces the system's ability to perform diagnostic tests on the transducer/blade system and to support troubleshooting in general.

Some limited diagnostic tests performed in the past involve sending a signal to the transducer to cause the blade to move and the system to be brought into resonance or some other vibration mode. The response of the blade is then determined by measuring the electrical signal supplied to the transducer when the system is in one of these modes. The ultrasonic system described in U.S. application Ser. No. 09/693,621, filed on Oct. 20, 2000, which is incorporated herein by reference, possesses the ability to sweep the output drive frequency, monitor the frequency response of the ultrasonic transducer and blade, extract parameters from this response, and use these parameters for system diagnostics. This frequency sweep and response measurement mode is achieved via a digital code such that the output drive frequency can be stepped with high resolution, accuracy, and repeatability not existent in prior art ultrasonic systems. However, if loss of lock occurs, no indication is made whether the hand piece, the generator or blade failure caused the fault. Further, this system lacks decisional circuitry for identifying and/or enunciating transducer/blade faults.

There are problems associated with the conventional ultrasonic surgical systems. For instance, some times the blades crack without the surgeon knowing because the cracks are very small. However, at high vibrations they can cause significant changes in operation and may create a safety issue. In addition, the transducer in the hand piece can fail. Thus, it is known in the art to conduct diagnostic tests to determine if the system is operating properly. Prior tests have involved merely indicated that a loss of lock has occurred, and no indication is made as to whether the hand piece, the generator or the blade cause the fault. Moreover, upon the occurrence of blade failures, no distinction is made between hand piece failures and blade failures.

SUMMARY OF THE INVENTION

The present invention is a method for distinguishing between bad hand pieces and blade failures in an ultrasonic surgical system. According to the invention, the rate of change of the resonance frequency and the rate of change of the resonance impedance of the hand piece/blade are monitored as the drive frequency is changed. As the system reaches resonance, the control system locks onto the resonance frequency. However, the control system causes the drive frequency to continue to change. When a loss of lock occurs with no recovery, the rate of change of the frequency and rate of change of the impedance are compared to obtain the fastest rate of change which is stored in non-volatile memory of the ultrasonic generator. If the rates of change are higher than the highest acceptable rates of change due to temperature changes with the longest blades, a "Bad Blade" message is displayed on an LCD.

The method of the invention permits the discrimination of a bad hand piece and a bad blade. This permits nurses and surgeons to promptly repair or replace the broken component by detecting, upon the loss of lock, whether the rate of change of impedance and frequency data is higher or lower than the values stored in memory for a good hand piece or blade.

BRIEF DESCRIPTION OF THE DRAWINGS

The foregoing and other advantages and features of the invention will become more apparent from the detailed description of the preferred embodiments of the invention given below with reference to the accompanying drawings in which.

DETAILED DESCRIPTION OF THE PREFERRED EMBODIMENTS

Figure 1:
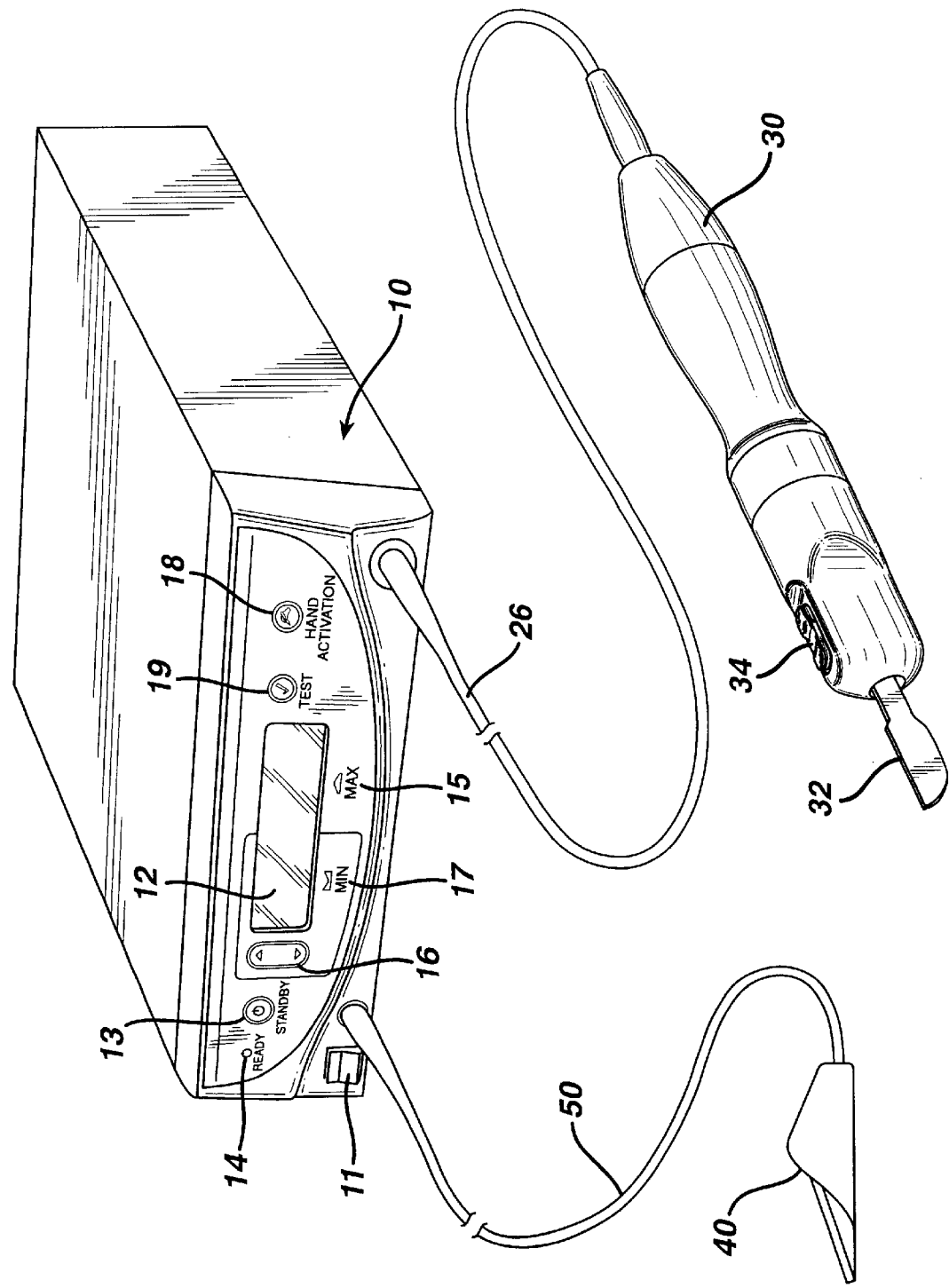
FIG. 1 is an illustration of a console for an ultrasonic surgical cutting and hemostasis system, as well as a hand piece and foot switch in which the method of the present invention is implemented.

FIG. 1 is an illustration of a system for implementing the method according to the invention. By means of a first set of wires in cable 20, electrical energy, i.e., drive current, is sent from the console 10 to a hand piece 30 where it imparts ultrasonic longitudinal movement to a surgical device, such as a sharp scalpel blade 32. This blade can be used for simultaneous dissection and cauterization of tissue. The supply of ultrasonic current to the hand piece 30 may be under the control of a switch 34 located on the hand piece, which is connected to the generator in console 10 via wires in cable 20. The generator may also be controlled by a foot switch 40, which is connected to the console 10 by another cable 50. Thus, in use a surgeon may apply an ultrasonic electrical signal to the hand piece, causing the blade to vibrate longitudinally at an ultrasonic frequency, by operating the switch 34 on the hand piece with his finger, or by operating the foot switch 40 with his foot.

The generator console 10 includes a liquid crystal display device 12, which can be used for indicating the selected cutting power level in various means such, as percentage of maximum cutting power or numerical power levels associated with cutting power. The liquid crystal display device 12 can also be utilized to display other parameters of the system. Power switch 11 is used to turn on the unit. While it is warming up, the "standby" light 13 is illuminated. When it is ready for operation, the "ready" indicator 14 is illuminated and the standby light goes out. If the unit is to supply maximum power, the MAX button 15 is depressed. If a lesser power is desired, the MIN button 17 is activated. The level of power when MIN is active is set by button 16.

When power is applied to the ultrasonic hand piece by operation of either switch 34 or 40, the assembly will cause the surgical scalpel or blade to vibrate longitudinally at approximately 55.5 kHz, and the amount of longitudinal movement will vary proportionately with the amount of driving power (current) applied, as adjustably selected by the user. When relatively high cutting power is applied, the blade is designed to move longitudinally in the range of about 40 to 100 microns at the ultrasonic vibrational rate. Such ultrasonic vibration of the blade will generate heat as the blade contacts tissue, i.e., the acceleration of the blade through the tissue converts the mechanical energy of the moving blade to thermal energy in a very narrow and localized area. This localized heat creates a narrow zone of coagulation, which will reduce or eliminate bleeding in small vessels, such as those less than one millimeter in diameter. The cutting efficiency of the blade, as well as the degree of hemostasis, will vary with the level of driving power applied, the cutting rate of the surgeon, the nature of the tissue type and the vascularity of the tissue.

Figure 2:
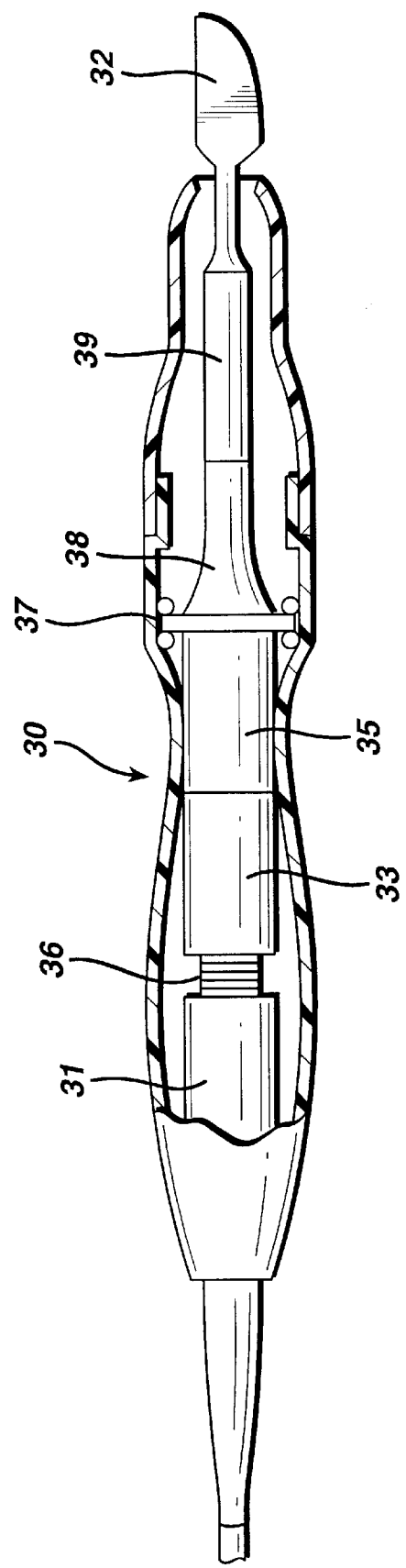
FIG. 2 is a schematic view of a cross section through the ultrasonic scalpel hand piece of the system of FIG. 1.

As illustrated in more detail in FIG. 2, the ultrasonic hand piece 30 houses a piezoelectric transducer 36 for converting electrical energy to mechanical energy that results in longitudinal vibrational motion of the ends of the transducer. The transducer 36 is in the form of a stack of ceramic piezoelectric elements with a motion null point located at some point along the stack. The transducer stack is mounted between two cylinders 31 and 33. In addition a cylinder 35 is attached to cylinder 33, which in turn is mounted to the housing at another motion null point 37. A horn 38 is also attached to the null point on one side and to a coupler 39 on the other side. Blade 32 is fixed to the coupler 39. As a result, the blade 32 will vibrate in the longitudinal direction at an ultrasonic frequency rate with the transducer 36. The ends of the transducer achieve maximum motion with a portion of the stack constituting a motionless node, when the transducer is driven with a maximum current at the transducers' resonant frequency. However, the current providing the maximum motion will vary with each hand piece and is a valve stored in the non-volatile memory of the hand piece so the system can use it.

The parts of the hand piece are designed such that the combination will oscillate at the same resonant frequency. In particular, the elements are tuned such that the resulting length of each such element is one-half wavelength. Longitudinal back and forth motion is amplified as the diameter closer to the blade 32 of the acoustical mounting horn 38 decreases. Thus, the horn 38 as well as the blade/coupler are shaped and dimensioned so as to amplify blade motion and provide harmonic vibration in resonance with the rest of the acoustic system, which produces the maximum back and forth motion of the end of the acoustical mounting horn 38 close to the blade 32. A motion at the transducer stack is amplified by the horn 38 into a movement of about 20 to 25 microns. A motion at the coupler 39 is amplified by the blade 32 into a blade movement of about 40 to 100 microns.

Figure 3A:
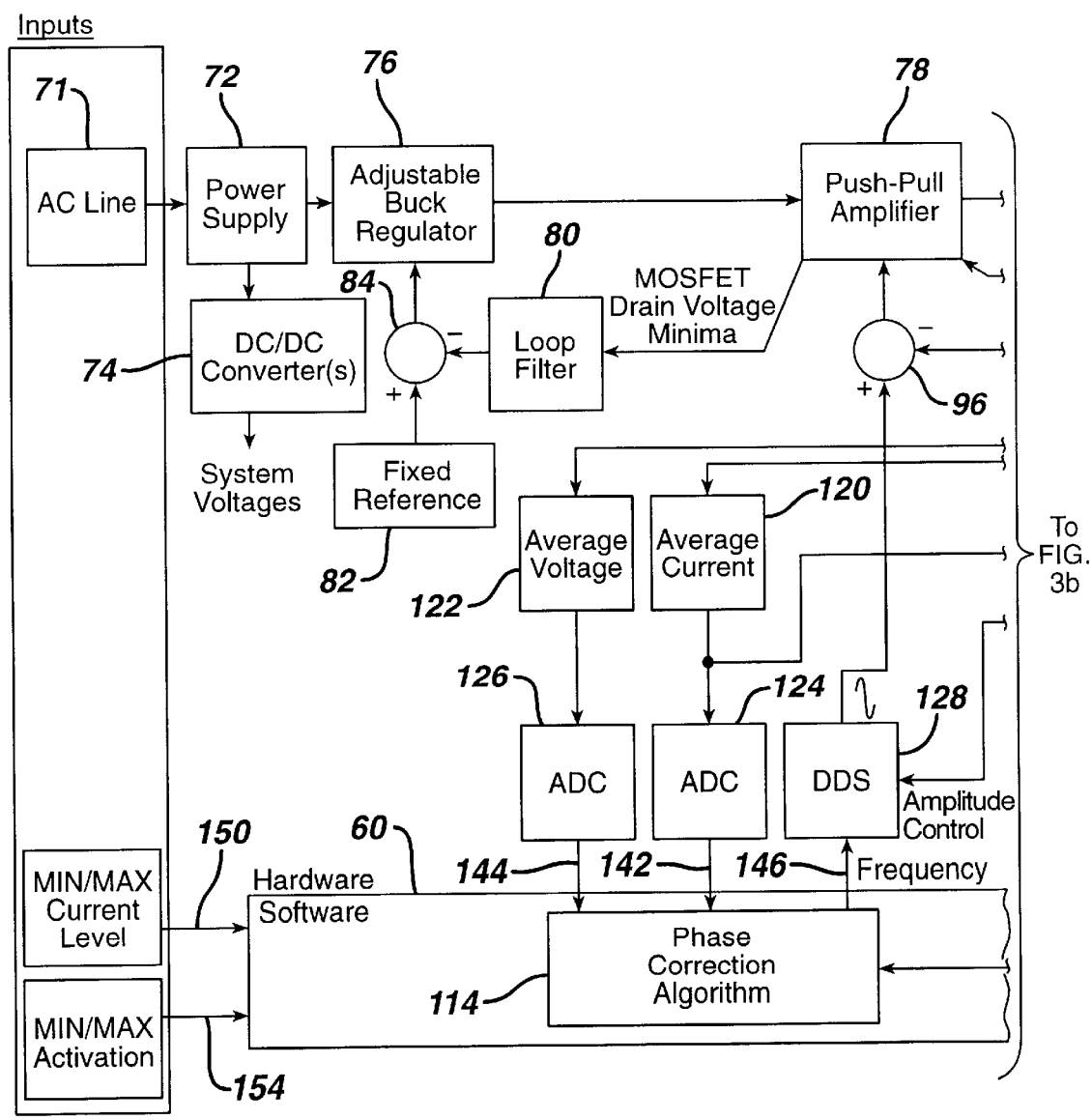
FIGS. 3(a) and 3(b) are block diagrams illustrating the ultrasonic generator in which the method of the invention is implemented.
Figure 3B:
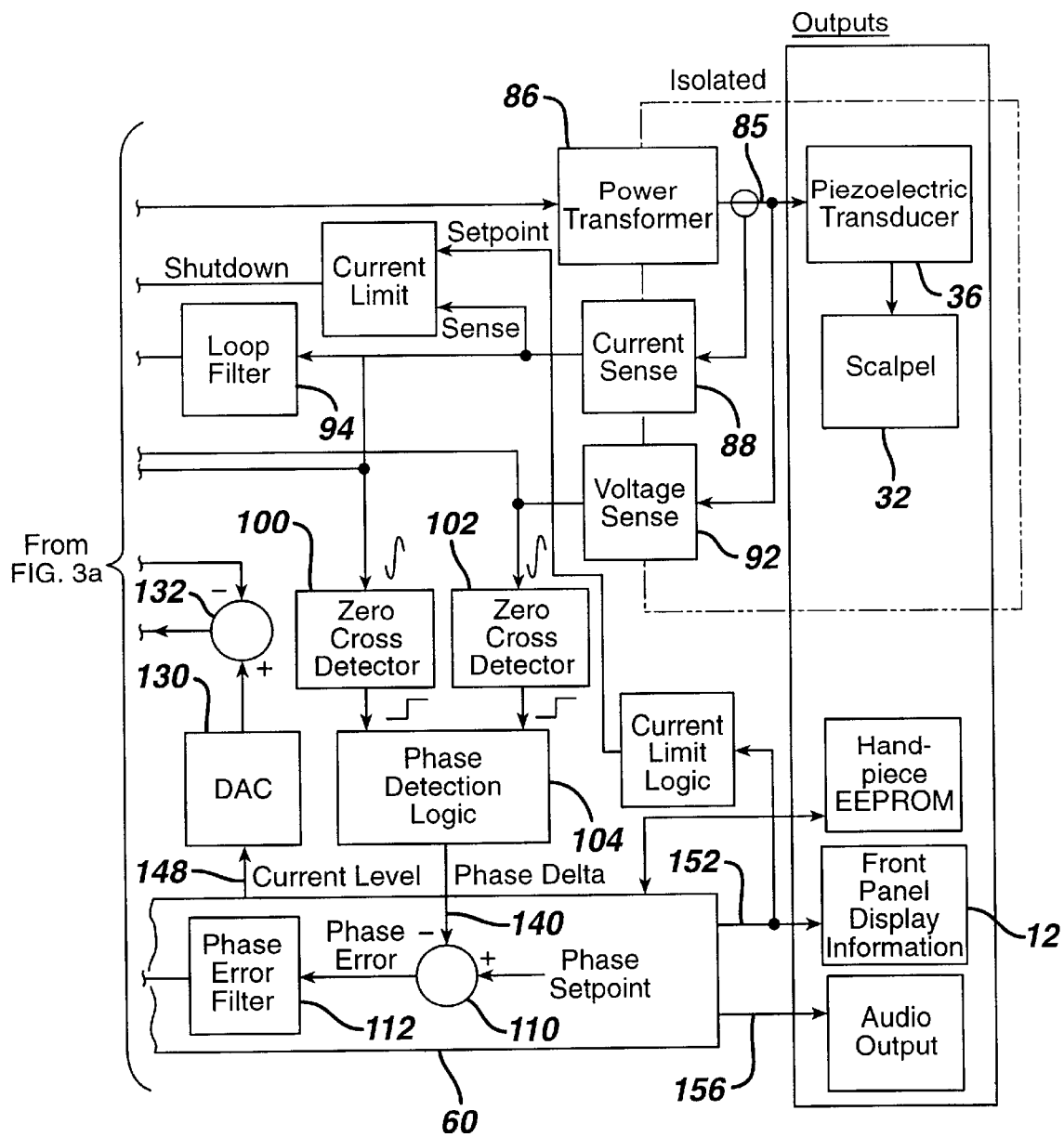

The system which creates the ultrasonic electrical signal for driving the transducer in the hand piece is illustrated in FIGS. 3(a) and 3(b). This drive system is flexible and can create a drive signal at a desired frequency and power level setting. A DSP 60 or microprocessor in the system is used for monitoring the appropriate power parameters and vibratory frequency as well as causing the appropriate power level to be provided in either the cutting or coagulation operating modes. The DSP 60 or microprocessor also stores computer programs which are used to perform diagnostic tests on components of the system, such as the transducer/blade.

For example, under the control of a program stored in the DSP or microprocessor 60, such as a phase correction algorithm, the frequency during startup can be set to a particular value, e.g., 50 kHz. It can than be caused to sweep up at a particular rate until a change in impedance, indicating the approach to resonance, is detected. Then the sweep rate can be reduced so that the system does not overshoot the resonance frequency, e.g., 55 kHz. The sweep rate can be achieved by having the frequency change in increments, e.g., 50 cycles. If a slower rate is desired, the program can decrease the increment, e.g., to 25 cycles which both can be based adaptively on the measured transducer impedance magnitude and phase. Of course, a faster rate can be achieved by increasing the size of the increment. Further, the rate of sweep can be changed by changing the rate at which the frequency increment is updated.

If it is known that there is a undesired resonant mode, e.g., at say 51 kHz, the program can cause the frequency to sweep down, e.g., from 60 kHz, to find resonance. Also, the system can sweep up from 50 kHz and hop over 51 kHz where the undesired resonance is located. In any event, the system has a great degree of flexibility In operation, the user sets a particular power level to be used with the surgical instrument. This is done with power level selection switch 16 on the front panel of the console. The switch generates signals 150 that are applied to the DSP 60. The DSP 60 then displays the selected power level by sending a signal on line 152 (FIG. 3(b)) to the console front panel display 12.

To actually cause the surgical blade to vibrate, the user activates the foot switch 40 or the hand piece switch 34. This activation puts a signal on line 154 in FIG. 3(a). This signal is effective to cause power to be delivered from push-pull amplifier 78 to the transducer 36. When the DSP or microprocessor 60 has achieved lock on the hand piece transducer resonance frequency and power has been successfully applied to the hand piece transducer, an audio drive signal is put on line 156. This causes an audio indication in the system to sound, which communicates to the user that power is being delivered to the hand piece and that the scalpel is active and operational.

Figure 4A:
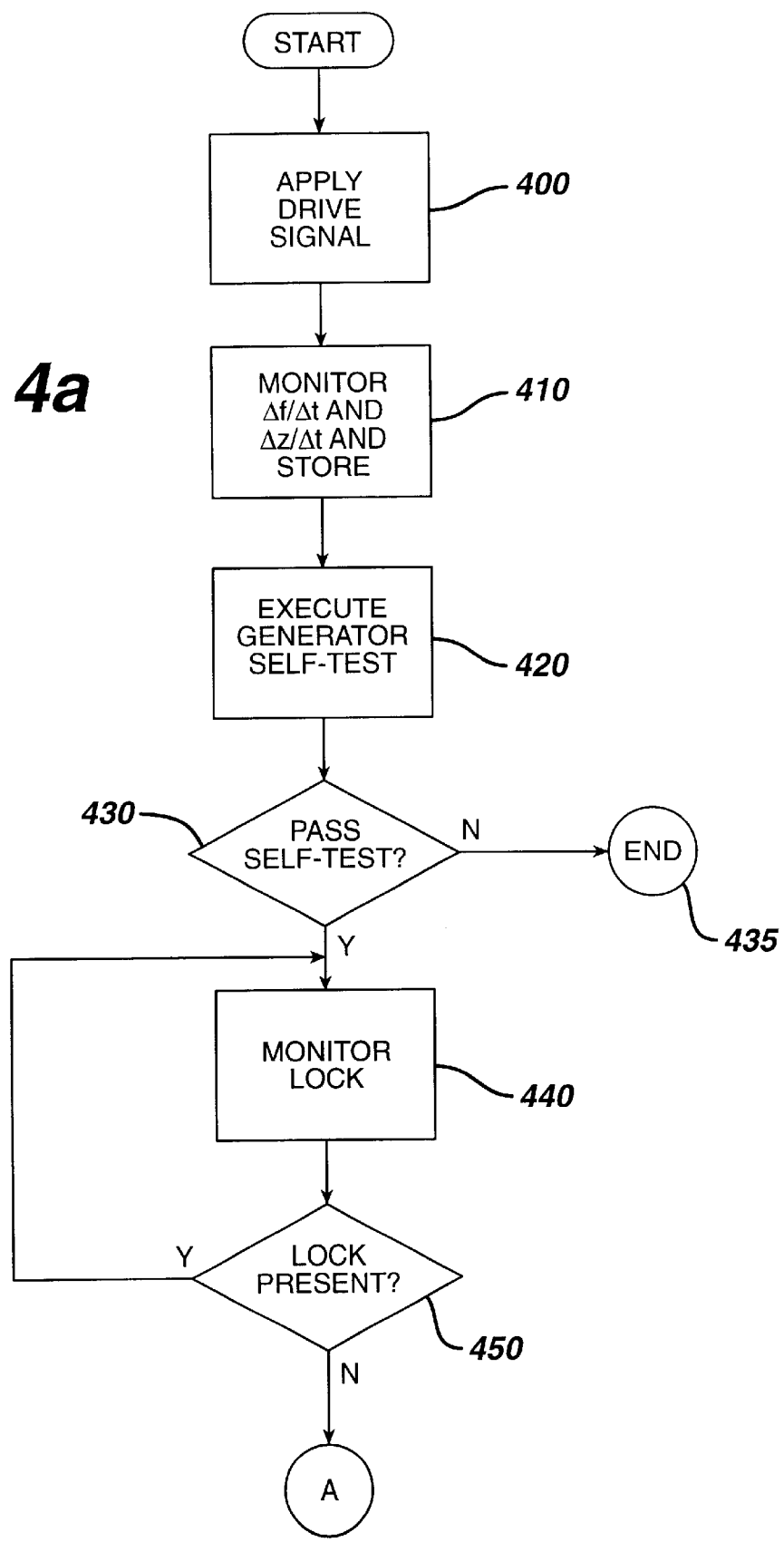
FIGS. 4(a) and 4(b) are flow charts illustrating a preferred embodiment of the invention.
Figure 4B:
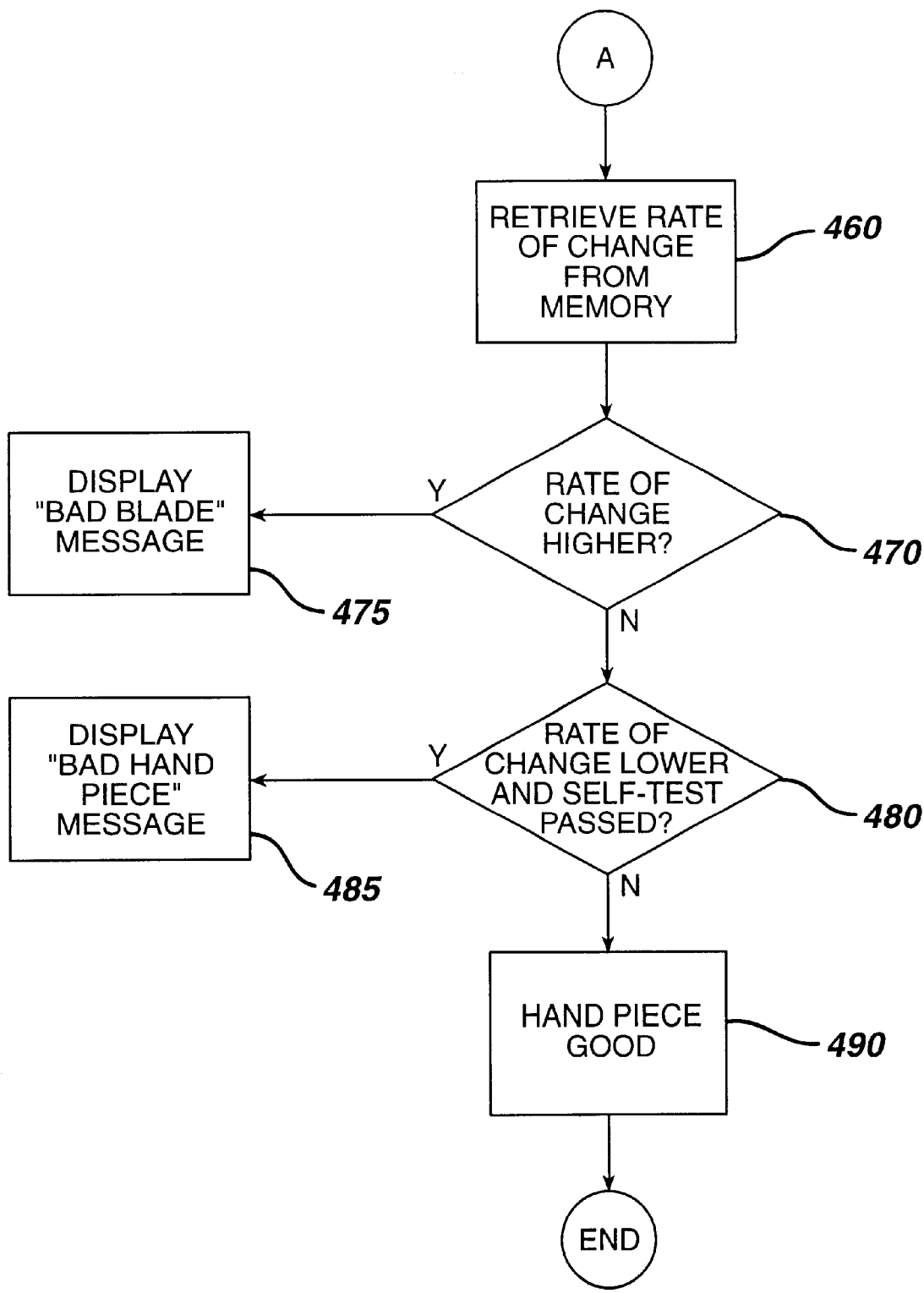

FIGS. 4(a) and 4(b) are flow charts illustrating the preferred embodiment of the invention. Under control of the program stored in the DSP or microprocessor 60 shown in FIGS. 3(a) and 3(b), the method of the invention is implemented by using the ultrasonic driver unit to excite the hand piece/blade and obtain impedance data over a frequency range of 50 to 56 kilohertz, as indicated in step 400.

Using the DSP to monitor the frequency, the rate of change of the resonance frequency ($\Delta f/\Delta t$) and resonance impedance ($\Delta z/\Delta t$) of the transducer/blade are continuously monitored. Selected values are stored in the non-volatile memory in the ultrasonic generator, as indicated in step 410. A generator diagnostic built-in-self-test is executed to check the status of internal circuitry within the generator, and a determination is made whether the generator passed the tests, as indicated in step 420.

The generator monitors ($\Delta f/\Delta t$) and ($\Delta z/\Delta t$) to determine whether lock is present, as indicated in step 450. Upon loss of lock with no recovery, a comparison of stored $\Delta f/\Delta t$ and $\Delta z/\Delta t$ values with defined thresholds is performed to determine whether the fastest rates of change observed exceed threshold values, as indicated in step 460.

If the fastest rates of change retrieved from memory are higher than the normally expected rates of change due to temperature changes associated with blades having the longest physical length, a "Bad blade" message is displayed on the LCD of the console, as indicated in step 475. If, on the other hand, the fastest rates of change retrieved from memory are lower than the normally expected rates of change due to temperature changes associated with blades having the longest physical length and the generator passed the built-in-self-test, a "Bad Hand piece" message is displayed on the LCD, as indicated in step 480. The normally expected rate of change is a value which is stored within the memory available to the generator, such as an EEPROM memory in a hand piece connected to the generator.

Using the method of the invention, rapid detection and isolation of bad hand pieces from bad blades are achieved, which result in an ease of use, and an increase of the diagnostic speed. As a result, it is easier for medical staff to act upon any fault conditions which may occur during use of the hand pieces or blades. It will be apparent to those skilled in the art that functions other than first derivatives may be used to perform the method of the present invention (for example, phase margin functions or second derivative functions).

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A method for distinguishing between bad hand pieces and blade failures in an ultrasonic surgical system, comprising the steps of:

applying a drive signal to an ultrasonic hand piece/blade at a predetermined drive frequency;

monitoring and storing a rate of change of a resonance frequency and a rate of change of a resonance impedance of the hand piece/blade as the drive frequency is changed in memory of the generator;

performing a diagnostic self test in an ultrasonic generator located in the ultrasonic surgical system;

monitoring the ultrasonic generator in the ultrasonic surgical system to determine whether lock is present;

if lock is not present, retrieving the rate of change of the resonance frequency and the rate of change of the resonance impedance from memory of the generator;

comparing the rate of change of the resonance frequency and the rate of change of the resonance impedance to obtain a fastest rate of change which is stored in the memory of the generator; and if the rates of change are higher than normal rates of change due to temperature changes associated with longer blades, displaying a message on a liquid crystal display of the generator.

2. The method of claims 1, wherein the step of applying the drive signal comprises exciting the hand piece/blade with an ultrasonic signal at the predetermined drive frequency.

3. The method of claim 2, wherein the predetermined drive frequency is in a range of 50 kHz to 56 kHz.

4. The method of claim 1, wherein the step of monitoring the rate of change of the resonance frequency and the rate of change of the resonance impedance is performed continuously at start up.

5. The method of claim 1, wherein, if the diagnostic self test fails, all tests are terminated.

6. The method of claim 1, wherein the step of monitoring the ultrasonic generator is performed during use of the hand piece/blade.

7. The method of claim 6, wherein use of the hand piece/blade comprises at least one of running the hand piece/blade in mid-air, cutting tissue, cauterizing tissue and coagulating tissue.

8. The method of claim 1, wherein the step of displaying the message comprises the steps of:

displaying a "Bad Blade" message on the liquid crystal display, if the rates of change are higher than the normal rates of change due to the temperature changes associated with the longer blades; and displaying a "Bad Hand Piece" message on the liquid crystal display, if the fastest rates of change are lower than the normally expected rates of change due to the temperature changes associated with the blades having the longest physical length and the generator passed the diagnostic self test.

9. The method of claim 8, wherein the normally expected rates of change are constant values which are stored in the memory of the generator.

* * * * *